United States Patent [19]

Michel

[11] Patent Number: 4,472,365

[45] Date of Patent: Sep. 18, 1984

[54] DICALCIUM PHOSPHATE DIHYDRATE HAVING IMPROVED MONOFLUOROPHOSPHATE COMPATIBILITY AND PROCESS FOR THE PREPARATION THEREOF

[75] Inventor: Christian G. Michel, Ossining, N.Y.

[73] Assignee: Stauffer Chemical Company, Westport, Conn.

[21] Appl. No.: 273,783

[22] Filed: Jun. 15, 1981

[51] Int. Cl.³ ............................................. C01B 25/32
[52] U.S. Cl. ................................... 423/267; 423/308; 423/309; 424/57
[58] Field of Search ...................... 423/308, 309, 267; 424/57

[56] References Cited

U.S. PATENT DOCUMENTS 2,869,987  1/1959  Horn ..................................... 423/637
2,869,988  1/1959  Gloss .................................... 423/637
4,312,843  1/1982  Monty et al. ......................... 423/309

FOREIGN PATENT DOCUMENTS 1548465  7/1979  United Kingdom .

OTHER PUBLICATIONS

Patent Application Serial No. 106,637, filed 12-26-79.
Kirk–Othmer, *Encyclopedia of Chemical Technology*, Second Edition, vol. 12, (1967), John Wiley and Sons, pp. 414–423.

*Primary Examiner*—John Doll
*Assistant Examiner*—Wayne A. Langel
*Attorney, Agent, or Firm*—Howard K. Kothe

[57] ABSTRACT

Dicalcium phosphate dihydrate composition having improved monofluorophosphate compatibility are prepared by the addition of magnesium oxide and pyrophosphoric acid to the reaction mixture, and terminating the reaction by which the dicalcium phosphate dihydrate is formed at a low pH.

6 Claims, No Drawings

DICALCIUM PHOSPHATE DIHYDRATE HAVING IMPROVED MONOFLUOROPHOSPHATE COMPATIBILITY AND PROCESS FOR THE PREPARATION THEREOF

BACKGROUND OF THE INVENTION

The present invention relates to dicalcium phosphate dihydrate compositions having improved monofluorophosphate compatibility, and to a process for the preparation thereof.

Dicalcium phosphate dihydrate has been used as a dental abrasive agent in toothpastes and powders for many years.

This material is typically produced by first reacting a slaked lime slurry with phosphoric acid to form a dicalcium phosphate dihydrate precipitate, and then separating the dicalcium phosphate dihydrate precipitate from the mother liquor after which it is dried and milled to form the final product as a fine powder.

One serious problem which was initially encountered in the use of dicalcium phosphate dihydrate in toothpaste was the tendency of the dicalcium phosphate dihydrate to "set-up" and become lumpy. When this occurs in toothpaste formulations, it makes it difficult to extrude the toothpaste from the tube in which it is usually packaged.

A second problem was encountered with the advent of the use of monofluorophosphate additives in toothpaste formulations. It was found that the monofluorophosphate components would react with the dicalcium phosphate whereby the monofluorophosphate component was converted from a water-soluble form to an insoluble form. Since the beneficial effect of monofluorophosphate additives in toothpaste are understood to be derived principally from the water-soluble form, it has become important to develop toothpaste formulations which permit an effective amount of monofluorophosphate component to remain in the water soluble state.

The term "monofluorophosphate-compatibility" has been used as a term-of-art to describe the tendency of such formulations to permit the monofluorophosphate component to remain in the water soluble state.

The monofluorophosphate compatibility and stability of dicalcium phosphate dihydrate in toothpaste formulations appear to be related in that the monofluorophosphate compatibility is affected by the stability. Improvements in stability generally result in improvements in monofluorophosphate compatibility.

The monofluorophosphate compatibility of a particular formulation may be determined by a variety of methods. Preferably, the monofluorophosphate compatibility of a formulation may be determined by actually preparing the formulation, placing it in storage for a predetermined period of time under controlled conditions, and then determining the amount of water-soluble monofluorophosphate which remains in the formulation after having been stored under these conditions. Alternatively, a simulated formulation, such as the dicalcium phosphate dihydrate to be tested, glycerine and a known amount of a monofluorophosphate component, such as sodium monofluorophosphate can be "quick aged" by maintaining at an elevated temperature for one or more hours, and the amount of water-soluble monofluorophosphate remaining after such conditioning then determined. There are, of course, many other methods for measuring the relative monofluorophosphate compatibility of various samples of dicalcium phosphate dihydrate.

U.S. Pat. No. 2,287,699 teaches that dicalcium phosphate dihydrate may be stabilized by adding a small amount of an alkali metal pyrophosphate to the mother liquor, at a controlled pH, during the preparation of the dicalcium phosphate. Specifically, it is taught that after precipitation of the dicalcium phosphate in the mother liquor, a small amount of alkali metal pyrophosphate should be added and the entire slurry then heated for a short period of time, while maintaining the pH of the mother liquor above 7.

Alternatively, the precipitate may be treated during the subsequent washing step.

It is also known to those skilled in the art that other forms of pyrophosphate can also be used to stabilize the dicalcium phosphate dihydrate.

Another method for stabilizing dicalcium phosphate dihydrate is disclosed in U.S. Pat. No. 2,018,410. This patent teaches that dicalcium phosphate can be stabilized by the addition thereto of a magnesium salt such as trimagnesium phosphate, magnesium sulfate, magnesium stearate, or dimagnesium phosphate.

Yet another method for stabilizing dicalcium phosphate dihydrate is disclosed in British Pat. No. 1,548,465. This patent teaches a process for stabilizing dicalcium phosphate dihydrate with the use of dimagnesium phosphate trihydrate, which comprises precipitating jointly with the dicalcium phosphate, or precipitating subsequently, directly onto the newly precipitated dicalcium phosphate dihydrate, dimagnesium phosphate trihydrate in an amount of 1 to 50% by weight of dicalcium phosphate dihydrate.

A complete solution to the problems presented by incompatibility between dicalcium phosphate dihydrate and monofluorophosphate additives in toothpastes however, has not yet been found, and the need for further improvements is well-recognized by the industry.

SUMMARY OF THE INVENTION

It has now been found that the addition of relatively small amounts of magnesium oxide to the reaction mixture during the preparation of dicalcium phosphate dihydrate can improve the monofluorophosphate compatibility of the final product.

In accordance with the present invention there is now provided a process for preparing dicalcium phosphate dihydrate compositions which have improved monofluorophosphate compatibility. This process comprises the steps of:

(1) reacting a slaked lime slurry with phosphoric acid to form a monocalcium phosphate solution;

(2) adding to the solution magnesium oxide, additional amounts of the slurry and from about 0.1% to about 1.0% pyrophosphoric acid, by weight of dicalcium phosphate dihydrate to be formed, to form a dicalcium phosphate dihydrate slurry having a pH ranging from about 4.9 to about 5.5;

(3) separating the dicalcium phosphate dihydrate from the slurry; and optionally (4) blending the dicalcium phosphate dihydrate with a stabilizing agent.

In a preferred embodiment, the monocalcium phosphate solution is formed, the magnesium oxide added, and then additional slaked lime slurry is added to the solution in an amount sufficient to form a dicalcium phosphate dihydrate slurry having a pH ranging from about 5.4 to about 5.9. Pyrophosphoric acid is then added in an amount sufficient to reduce the pH to from about 4.9 to about 5.5; provided, however, that the amount of pyrophosphoric acid so added is at least 0.1% by weight of dicalcium phosphate dihydrate to be produced. The process, in accordance with this preferred embodiment may therefore be defined as:

(1) reacting a slaked lime slurry with phosphoric acid to form a monocalcium phosphate solution;
(2) adding magnesium oxide into the solution and adding additional slaked lime slurry in an amount sufficient to form a dicalcium phosphate dihydrate slurry having a pH ranging from about 5.4 to about 5.9;
(3) adding into the dicalcium phosphate dihydrate slurry an amount of pyrophosphoric acid sufficient to reduce the pH of the slurry to from about 4.9 to about 5.5 provided, however, that the minimum amount of pyrophosphoric acid so added is at least 0.1% by weight of dicalcium phosphate dihydrate.
(4) separating the dicalcium phosphate dihydrate from the slurry.

DETAILED DESCRIPTION OF THE INVENTION

In preparing the dicalcium phosphate dihydrate composition of the present invention, the pyrophosphoric acid and lime slurry added in the second step may be added in any order, so long as the terminal pH of this step is within the specified limits, but it is preferable that the magnesium oxide be added before the additional lime slurry.

The lime which is used in the practice of the present invention is the same type rotary kiln lime or shaft kiln lime as is used in conventional dicalcium phosphate processes.

The slaked lime slurry is prepared by mixing lime with either water or recycled mother liquor (i.e., that which remains after removal of the dicalcium phosphate dihydrate product from the final slurry), or both, in amounts of from about 100 to about 150 grams CaO/liter and at a temperature preferably ranging from about 70° C. to about 74° C. At higher concentrations the mixture will become a gelatinous mass which will be difficult to handle, while at concentrations below the range specified the process "payload" will be unnecessarily reduced.

The slaked lime slurry is then added to phosphoric acid to form a monocalcium phosphate solution.

The acid which is used is preferably a food grade phosphoric acid, preferably at an initial concentration of about 85%. Varying amounts of recycled mother liquor may also be added to the lime slurry and phosphoric acid, with the specific amount in each case being determined in accordance with the preferences of the individual practitioner. The compositional range of the monocalcium phosphate solution will be approximately as follows:

| | Amount | |
|---|---|---|
| | High (Wt. %) | Low (Wt. %) |
| CaO | 4 | 2 |
| $P_2O_5$ | 22 | 12 |
| pH | 2 | 1 |

These ranges are set forth as examples of those which are typical, and are in no way intended to be limitations on the scope of the present invention. Those skilled in the art will understand that higher and lower amounts may also be used, provided that the reaction mixture meets the requirements of the practitioner.

When the lime slurry and phosphoric acid are brought together under the conditions specified above, a reaction will ensue and a monocalcium phosphate solution will be formed. The essential completion of the reaction will be indicated by a steady-state pH of from about 1.0 to about 2.0.

The preparation of the monocalcium phosphate solution can be carried out as a continuous, batch or semi-batch process.

The magnesium oxide is then preferably added to the monocalcium phosphate solution either before the additional slaked lime slurry is added, or during the addition. The magnesium oxide is preferably added when the pH is in the range of from about 1 to about 4, with the lower end of the pH range being particularly preferred. Although not preferred, addition of the magnesium oxide could also be accomplished by adding it directly to the phosphoric acid, or even to the slaked lime slurry itself.

The amount of magnesium oxide added is quite small, and generally ranges from about 0.05 to about 0.5% by weight calcium oxide, although greater amounts could be added without harm. Where process streams, such as mother liquor, are recycled in the process, some of the magnesium oxide (although not necessarily in the form of magnesium oxide or hydroxide) can be recycled with the recycle stream, thereby reducing the amount of fresh magnesium oxide which must be added to maintain acceptable levels within the process. The appropriate "steady state" conditions can easily be established for any particular process configuration by routine experimentation.

Once the monocalcium phosphate solution has been formed, the pyrophosphoric acid and additional slaked lime are added to form the dicalcium phosphate dihydrate slurry. This reaction is exothermic and external cooling is required to control the reaction temperature. The reaction temperature should be controlled at or below about 45° C. At temperatures above about 45° C. anhydrous dicalcium phosphate crystals may be formed.

It is preferable to first add the additional slaked lime slurry to the monocalcium phosphate solution in an amount sufficient to form a slurry having a pH ranging from about 5.4 to about 5.9, although a pH of 5.7 is most preferred. Once the specified pH is achieved, on a steady-state basis, in this preferred embodiment, the pyrophosphoric acid is added in an amount sufficient to reduce the pH to a pH ranging from about 4.9 to about 5.5, although a pH of from about 5.2 to about 5.4 is preferred and a pH of 5.3 is most preferred. The minimum amount of pyrophosphoric acid which should be added is about 0.1% by weight of dicalcium phosphate dihydrate to be prepared while the maximum required should be about 1.0%.

Although it is preferable to add the pyrophosphoric acid and slaked lime slurry to the monocalcium phosphate solution in the sequence just described, it is within the scope of the invention to add these two ingredients in other than that sequence. It is, however, important that the terminal pH, after both of these ingredients are added, ranges from about 4.9 to about 5.5 and preferably, that it be about 5.3.

It is, for example, within the scope of the present invention to add the pyrophosphoric acid before the additional slaked lime slurry, or together with the slaked lime slurry. The amount of pyrophosphoric acid added should range from about 0.1% to about 1.0%, by weight of dicalcium phosphate dihydrate to be produced, and preferably, from about 0.3% to about 0.4%.

Once the dicalcium phosphate dihydrate slurry has been formed as described above, the dicalcium phosphate dihydrate product is separated from the mother liquor. The mother liquor may then be recycled to the beginning of the process, or discarded.

The separation of the dicalcium phosphate dihydrate from the slurry can be accomplished by any of several conventional techniques. These techniques include, but are not limited to, decantation, centrifugation, filtration and the like, although decantation is preferred because of its simplicity.

Once the dicalcium phosphate dihydrate is separated from the slurry, it can be dried, milled and mixed with a stabilizer.

The stabilizers which can be added to dicalcium phosphate dihydrate are intended to prevent the "caking" and "lumping" which occurs in unstabilized dicalcium phosphate dihydrate as a result of dehydration. These are many stabilizers known to be useful for this purpose. These include, but are not limited to dimagnesium phosphate, trimagnesium phosphate, magnesium stearate and magnesium sulfate. The amount of stabilizer added ranges from about 0.5% to about 5.0% by weight of dicalcium phosphate dihydrate. Preferred stabilizers for use in the practice of the present invention are dimagnesium phosphate trihydrate, trimagnesium phosphate octahydrate, and mixtures thereof.

It is preferred to add the stabilizer to the dicalcium phosphate dihydrate by dry-blending these two components after the dicalcium phosphate dihydrate has been dried or after it has been dried and milled. It is, however, within the scope of the invention to add the stabilizer to the product slurry before separating the dicalcium phosphate dihydrate therefrom; or to the "wet" dicalcium phosphate dihydrate prior to drying and milling.

I claim:

1. A process for preparing dicalcium phosphate dihydrate compositions having improved monofluorophosphate compatibility which comprises the steps of:
   (a) reacting a slaked lime slurry with phosphoric acid to form a monocalcium phosphate solution;
   (b) adding to said solution magnesium oxide and additional amounts of said lime slurry and from about 0.1% to about 1.0% pyrophosphoric acid, by weight of dicalcium phosphate dihydrate to be formed, to form a dicalcium phosphate dihydrate slurry having a pH ranging from about 4.9 to about 5.5, said magnesium oxide being added in an amount ranging from about 0.05 to 0.5% by weight of calcium oxide;
   (c) separating the dicalcium phosphate dihydrate from said slurry; and optionally
   (d) blending said dicalcium phosphate with a stabilizing agent.

2. The process of claim 1 wherein said pH is about 5.3.

3. A process for preparing dicalcium phosphate dihydrate compositions having improved monofluorophosphate compatibility which comprises the steps of:
   (a) reacting a slaked lime slurry with phosphoric acid to form a monocalcium phosphate solution;
   (b) adding into said solution magnesium oxide and additional slaked lime slurry to form a dicalcium phosphate dihydrate slurry having a pH ranging from about 5.4 to about 5.9;
   (c) adding into said dicalcium phosphate dihydrate slurry an amount of pyrophosphoric acid sufficient to reduce the pH of said slurry to from about 4.9 to about 5.5 provided, however, that the minimum amount of pyrophosphoric acid so added is at least 0.1% by weight of dicalcium phosphate dihydrate;
   (d) separating said dicalcium phosphate dihydrate from said slurry; and optionally
   (e) blending said dicalcium phosphate dihydrate with from about 0.5% to about 5% by weight of the dicalcium phosphate dihydrate of dimagnesium phosphate, trimagnesium phosphate or mixtures thereof.

4. The process of claim 3 wherein said pH in step "b" is 5.7.

5. The process of claim 4 wherein said pH of step "c" is 5.3.

6. The process of claim 5 wherein said dicalcium phosphate dihydrate is blended with trimagnesium phosphate.

* * * * *